United States Patent
Haddock

(10) Patent No.: US 8,023,121 B2
(45) Date of Patent: Sep. 20, 2011

(54) METHOD FOR OPTICALLY COLLECTING NUMISMATIC DATA AND ASSOCIATED ALGORITHMS FOR UNIQUE IDENTIFICATION OF COINS

(75) Inventor: Richard M. Haddock, Redwood City, CA (US)

(73) Assignee: CoinSecure, Inc., Palo Alto, CA (US)

( * ) Notice: Subject to any disclaimer, the term of this patent is extended or adjusted under 35 U.S.C. 154(b) by 248 days.

(21) Appl. No.: 12/426,883

(22) Filed: Apr. 20, 2009

(65) Prior Publication Data

US 2009/0284754 A1 Nov. 19, 2009

Related U.S. Application Data

(60) Provisional application No. 61/046,347, filed on Apr. 18, 2008.

(51) Int. Cl.
G01B 11/24 (2006.01)
G01B 11/28 (2006.01)

(52) U.S. Cl. ........ 356/601; 356/614; 356/630; 194/302; 194/318

(58) Field of Classification Search .... 356/237.1–237.5, 356/337, 601–623, 630–632; 194/302, 328, 194/318, 334
See application file for complete search history.

(56) References Cited

U.S. PATENT DOCUMENTS

| | | | |
|---|---|---|---|
| 4,899,392 A | 2/1990 | Merton | |
| 5,133,019 A | 7/1992 | Merton et al. | |
| 5,224,176 A * | 6/1993 | Crain | 382/136 |
| 5,694,214 A | 12/1997 | Watanabe et al. | |
| 6,262,432 B1 | 7/2001 | Brunfeld et al. | |
| 6,328,150 B1 | 12/2001 | Hibari | |
| 6,685,000 B2 | 2/2004 | Sugata et al. | |
| 6,763,148 B1 | 7/2004 | Sternberg et al. | |
| 6,768,983 B1 | 7/2004 | Jakatdar et al. | |
| 7,271,918 B2 | 9/2007 | DeGroot et al. | |
| 7,324,214 B2 | 1/2008 | DeGroot et al. | |
| 2002/0154290 A1* | 10/2002 | Tompkin et al. | 356/71 |
| 2006/0103855 A1 | 5/2006 | Hazart | |
| 2007/0097380 A1 | 5/2007 | DeGroot et al. | |
| 2009/0135426 A1* | 5/2009 | Bell et al. | 356/445 |
| 2009/0295912 A1* | 12/2009 | Haddock | 348/61 |
| 2009/0303478 A1* | 12/2009 | Haddock | 356/337 |
| 2010/0039818 A1* | 2/2010 | Haddock | 362/253 |

FOREIGN PATENT DOCUMENTS

| | | |
|---|---|---|
| EP | 0439669 A2 | 8/1991 |
| EP | 1067485 A1 | 1/2001 |
| GB | 2248333 A | 4/1992 |

* cited by examiner

*Primary Examiner* — Hoa Pham
(74) *Attorney, Agent, or Firm* — Schneck & Schneck; David M. Schneck

(57) ABSTRACT

A method to generate an optical signature of a coin is disclosed. A plurality of parameters are generated and recorded related to rotational positions around the circumference of a coin. The data from these parameters are combined to produce a searchable value.

20 Claims, 2 Drawing Sheets

METHOD FOR OPTICALLY COLLECTING NUMISMATIC DATA AND ASSOCIATED ALGORITHMS FOR UNIQUE IDENTIFICATION OF COINS

CROSS-REFERENCE TO RELATED APPLICATION

This application claims priority from provisional application Ser. No. 61/046,347, filed Apr. 18, 2008.

TECHNICAL FIELD

The present invention relates generally to coin collecting and valuation of coins, and more particularly, to a method and resulting file structure to uniquely identify data files associated with coin light scattering measurement.

BACKGROUND

The interest in the collection and conservation of coins and related objects has been historically considered a personal interest activity, with little formal standards or controls concerning the trading of coins. The recent rise in the value of coins compared to earlier levels has promoted the trading of coins to a higher degree of professional structure, most significantly by the advent of commercial third party coin grading services who have developed systems to apply a widely accepted quality grade (based on a numerical scale from 1 to 70 with 70 being the highest quality). After examining and determining the grade of a coin, the commercial services place the coin in a clear plastic holder in which a grade label with a reference barcode is affixed. The clear plastic holder is then ultrasonically welded around the coin, thus permanently linking the grade to the coin within the case. A barcode is linked to the database which can be searched to confirm that the referenced coin was graded by the commercial service, along with some additional transaction details such as the date, place, company grading the coin, etc.

The grading service charges a fee for the provided services and gives a warranty of grading accuracy as part of the transaction value. The result of this commercial service is to allow the plastic encapsulated coins to be more readily traded as their trade value is directly linked to the professional quality grade shown on the plastic holder.

However, the current commercial grading services can lack repeatability and consistency. Further, current services are unable to prevent "grader shopping" in which a coin owner may specifically hunt for the highest value for a given coin by removing the coin from the plastic holder and re-submitting it since there is currently not a mean to identify a specific coin outside of the labeled box or other rigorous objective means for identifying a specific coin.

Any such objective means for coin grading would require a method to compare coin specific physical data for the identification of coins.

SUMMARY

In various exemplary embodiments, a method to identify coins is disclosed, in which data from various sources is used to provide a data signature of a coin based on uniquely detectable physical properties.

BRIEF DESCRIPTION OF THE DRAWINGS

The appended drawings illustrate exemplary embodiments of the present invention and must not be considered as limiting its scope.

DETAILED DESCRIPTION

The use of one or more sensors capable of making automated quantitative measurements of various physical characteristics of coins are combined using one or more mathematical equations to distill, display, and store the quantitative measurements into a single digital file. The digital file represents the identification of the measured coin. Moreover, the digital file is structured allowing an efficient means of searching a high volume of files of other coin data to find the file of a particular coin should the coin be re-analyzed at a future date.

The coin identification algorithms described herein allows development of a complete coin identification system, thus adding value to the sale and ownership of coins for both personal and commercial uses. Coin identification, as noted herein, uses a system architecture configured to accurately and repeatably generate light scattering measures or/and surface profilometry measurements based upon physical properties of any given coin. Either manipulated or raw measurement data from these measurements are captured and stored into one or more digital files.

A mathematical algorithm, described below, is applied to reduce the data into a single identification template file. The template file is referred to as a "CoinPrint" herein. The CoinPrint file is then stored in any appropriate database (e.g., any number of digital, optical, or other storage systems known in the art including hard drives and hard drive arrays, CD-ROM or DVD discs, etc.) that allows subsequent searching and retrieval of CoinPrint templates.

A simple and intuitive user interface allows both capture of data from coins and searching and retrieval for conducting searches of previously scanned coins. A design for the user interface is known in the art and may be readily produced by applying principles and algorithms described herein.

Figure 1A:
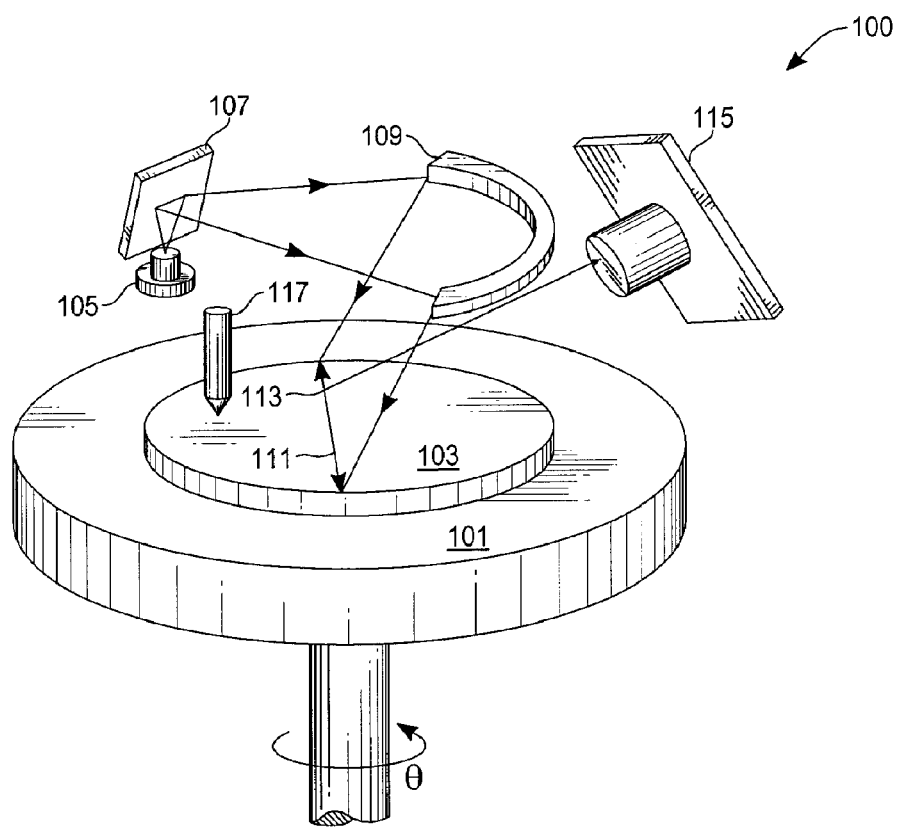
FIG. 1A is an exemplary embodiment of a simplified schematic of an optical light scattering apparatus for characterizing coins.

With reference to FIG. 1A, an exemplary embodiment of a simplified schematic of an optical scattering apparatus 100 includes a rotating sample platform 101 configured to accept coins undergoing measurement, a sample coin 103, and a light source 105. The light source 105 may be a laser, light-emitting diode (LED), a broadband light source, or a variety of light-producing sources (or other sources producing electromagnetic energy) known in the art. In a specific exemplary embodiment, the light source 105 includes a plurality of LEDs, at least one each to generate the primary spectrum of red, green, and blue (RGB).

The optical scattering apparatus 100 further includes beam forming optics (not shown but known in the art), allowing a line of light to form on a steering mirror 107. The steering mirror 107 may be a vibrating front-surface mirror, a rotating polygonal mirror, or any number of beam-steering types of optics for producing a line of light. A telecentric scanning mirror 109 may optionally be used in conjunction with or in place of the steering mirror 107 and the beam forming optics directing a line of light 111 across the surface of the sample coin 103. At a predefined point 113 on a surface of the sample coin 103, an intensity measurement is taken by a sample imaging optic 115.

The sample imaging optic 115 may be, for example, a lens or another light collection element optical train or single optical element placed in front of a CMOS sensor or CCD sensor array. In other embodiments, the sample imaging optic 115 may be either a single sensor or a group of sensors. In any case, the sample imaging optic 115 is configured to record a plurality of intensity measurements of either scattered or reflected light from the surface of the sample coin 103, all in one or more colors or, alternatively, a grey-scale intensity. At least one "point" (e.g., a pixel) of light will be imaged from the predefined point 113. As the sample coin 103 is rotated through a 360° arc, the predefined point 113 traces a circle on the surface of the sample coin 103.

With continuing reference to FIG. 1A, the optical scattering apparatus 100 further includes an automatic focusing element 117. Although shown as a separate element, the automatic focusing element 117 may be incorporated as a portion of the light source 105. Automatic focusing (AF) lenses and related systems are known in the art and may be employed to keep an output beam focused as the beam is directed over the topography of a typical coin. Automatic focusing is not required in many configurations, such as when using a laser light source. The absolute thickness and thickness variation measurements of the sample coin 103 could also be determined (e.g., as measured with reference to a height of the coin measured in reference to a height of the rotating sample platform 101) by noting electrical current present in AF coils. Thus, the automatic focusing element 117 serves as a type of optical profilometer. A spatial frequency (i.e., an inverse spatial wavelength) and a resulting spatial bandwidth may be determined based upon a focused beam diameter and a maximum scan length of the beam over the surface of the sample coin 103.

Figure 1B:
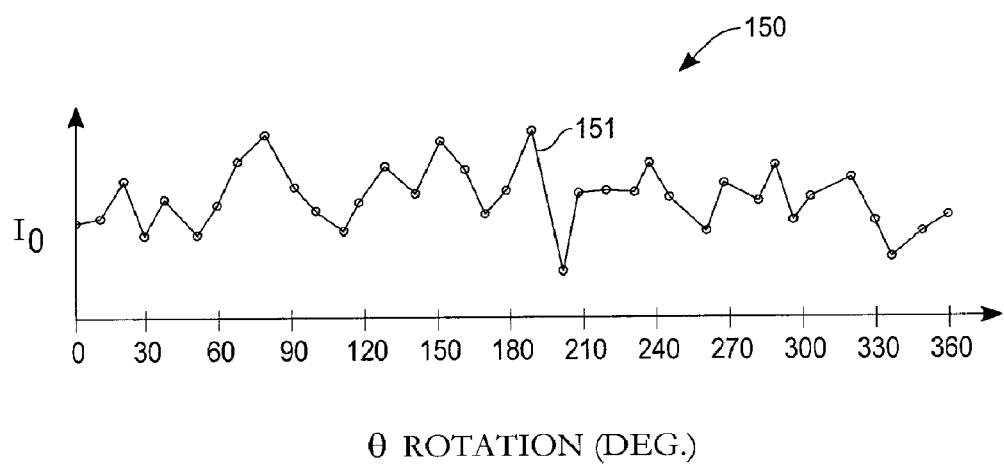
FIG. 1B is an exemplary histogram obtained from a physical defect sensor used in conjunction with the light scattering apparatus of FIG. 1A.

With reference now to FIG. 1B, an intensity plot 150 shows a recorded output 151 of intensity level from the sample imaging optic 115. One parameter that may be extracted from the sample imaging optic 115 is a physical defect sensor (PDS) mapping of intensity mapping due to surface damage of the sample coin 103. The surface damage may be caused by scratches, dents, or other random surface variations. The recorded PDS output may be sampled at a number of locations. In a specific exemplary embodiment, a maximum intensity level of the recorded output 151 is sampled each 10° of rotation. Thus, 36 independent values of intensity level are recorded by this scheme. One unique parameter used in the labeling and retrieval algorithm, discussed in more detail below, consecutively lists each of the 36 values from the PDS mapping as:

$$PDS = n_{p1}, n_{p2}, n_{p3}, \ldots, n_{p36}$$

Figure 2:
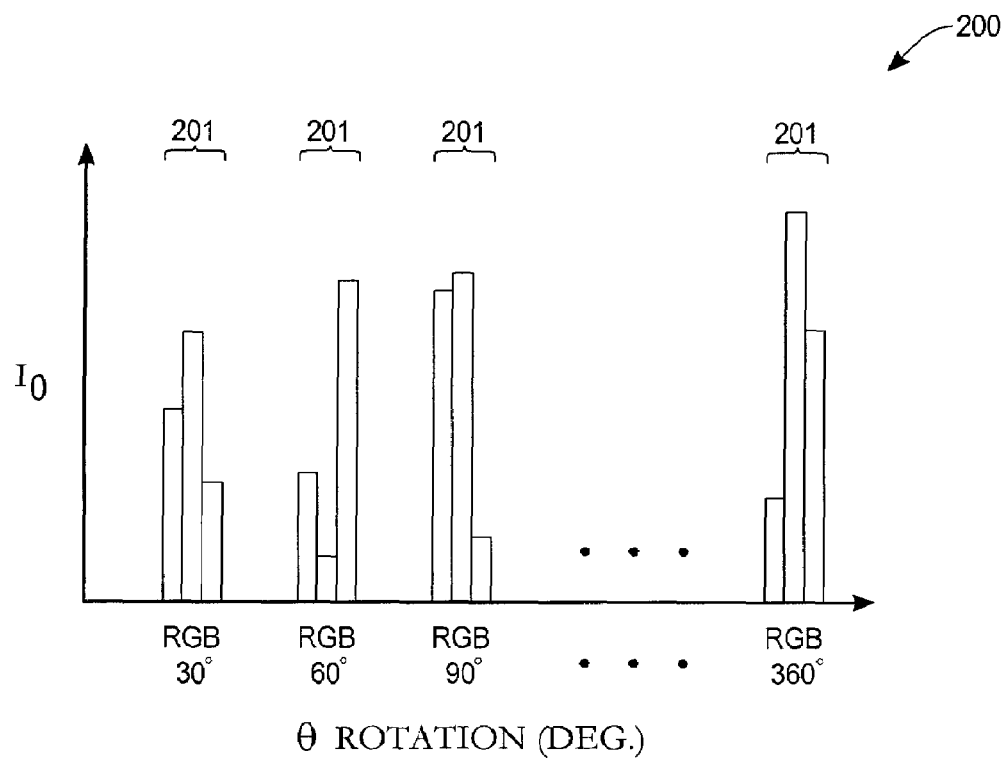
FIG. 2 is an exemplary color histogram obtained from a color sensor used in conjunction with the scattering apparatus of FIG. 1A.

With reference to FIG. 2, an exemplary surface color histogram 200 displays an intensity level for each of the three LEDs or other tri-color light sources as collected from the surface of the sample coin 103 (FIG. 1A). In this exemplary embodiment, the intensity level for each group of three colors 201 is recorded at 30° increments.

The intensity levels are collected in a similar fashion as the total intensity levels of FIG. 1A. However, the exemplary surface color histogram 200 displays an intensity level for each RGB light source. Alternatively, if the optical scattering apparatus 100 uses a broadband or white light source, the exemplary color histogram 200 is displaying an intensity level for each RGB sensor on, for example, a color CMOS or CCD display.

Thus, taking one RGB measurement every 30° produces 12 independent values of three measurements each. Thus, a second unique parameter used in the labeling and retrieval algorithm lists each of the 12 values from the surface color histogram (SCH) as:

$$SCH = n_{s1}, n_{s2}, n_{s3}, \ldots, n_{s12}$$

where each value, $n_{sx}$, represents three separate values.

Figure 3:
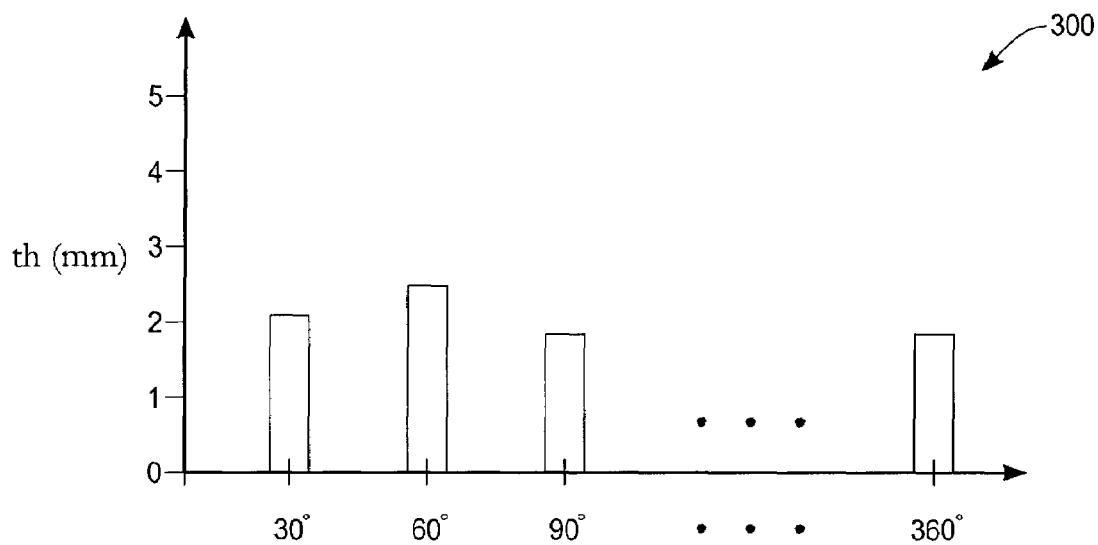
FIG. 3 is an exemplary coin thickness histogram obtained from a thickness monitor used in conjunction with the scattering apparatus of FIG. 1A.

FIG. 3 is a thickness graph 300 showing coin thickness as a function of rotational angle. The thickness graph in the exemplar shows a thickness value recorded every 30° of rotation. Values of thickness are measured using current readings from the automatic focusing element 117 (FIG. 1A). A skilled artisan will recognize how to calibrate and convert the current readings into thickness measurements.

Similar to the manner with which PDS and SCH are recorded, a coin thickness measurement (CTM) taken every 30° produces 12 independent values. A third unique parameter used in the labeling and retrieval algorithm lists each of the 12 values from CTM as:

$$CTM = n_{c1}, n_{c2}, n_{c3}, \ldots, n_{c12}$$

An exemplary algorithm for producing a CoinPrint template value thus uses the physical parameters (i.e., measurements) from a particular coin is used to derive a unique value for each and every coin scanned. The algorithm is thus designed to be scalable to take inputs from a plurality of different sensors (or different portions or values from a single sensor), each potentially having very diverse file structures, and reducing each of these values into a simple template file name. The template file name is therefore representative of several physical measurement values.

A CoinPrint template value is therefore a function of the three parameters selected and may take the form of:

$$CPT = f[(\alpha \cdot PDS) + (\beta \cdot SCH) + (\phi \cdot CTM)]$$

An actual file name may be constructed in accordance with the functional relationship of three parameters as stated above. In a specific exemplary embodiment, after substituting the individual measurement values, the file name may take the form of:

$$CPTF_{(1)} = \begin{bmatrix} (\alpha \cdot n_{p1}, n_{p2}, n_{p3}, \ldots, n_{p36}) + \\ (\beta \cdot n_{s1}, n_{s2}, n_{s3}, \ldots, n_{s12}) + \\ (\phi \cdot n_{c1}, n_{c2}, n_{c3}, \ldots, n_{c12}) \end{bmatrix}$$

As will be immediately recognizable by a skilled artisan, values for each of the constants $\alpha, \beta,$ and $\phi$ may be selected in a variety of ways. Each of the constant values may be selected to be any real number, including integers and real values, both greater than or less than "1." The number of significant figures is chosen such that at least one significant figure exists for each of an anticipated number of coins that are scanned, stored, and retrievable from a database. For example, if an anticipated number of coin templates to be stored is one billion (i.e., $1 \times 10^8$), then a value of CPTF is selected to have at least 8 significant figures.

In another specific exemplary embodiment, the CoinPrint template output file may optionally take the form of $$CPTF_{(2)} = PDSxxxxxxxx.SCHyyyyyyyy.CTMzzzzzzzz$$

thus retaining parseable, discrete values for each of the three measured parameters.

One specific benefit of the CPTF value is creation of a file template structure, capable of being parsed, and allowing a flexible application of both contemporary and future sensor configurations in a scattering coin apparatus. The algorithm structure defined herein further allows backward compatibility in the future when correlating files with sensor measurements taken today.

The search algorithm may therefore parse the CoinPrint template database file to separate individual reduced sensor values allowing parallel and independent database searches of each parameter. The output file is then constructed from the best matches of the individual parameter factors by cross-matching to parallel parameter files.

An exemplary file structure may be maintained on either a local or remote database as shown in Table 1, below.

TABLE 1

| Record No. | $CPTF_{(1)}$ Value | Coin Grading Barcode | Date Recorded | Other Comments |
|---|---|---|---|---|
| 0001 | 12305243 | 1257895 | Dec. 31, 2008 | note 1 |
| 0002 | 17585521 | 1585934 | Nov. 11, 2008 | note 2 |
| 0003 | 99812220 | 1998246 | Apr. 18, 2008 | note 3 |

Alternative coin scanning systems exist, such as those shown in co-pending provisional patent application 61/046,336, hereby expressly incorporated by reference for all purposes herein. This system illustrates a device for detecting light scattering from a coin surface. This scattering is detected in eight channels by eight pairs of photo detectors in a linear detector array. An optical encoder correlates the detection data with the rotation of a coin on a turntable. 2500 readings are made during a single rotation. The resulting information may be stored in tabular form: columns 1-8 for each pair of detectors and rows 1-2500 storing the reading at each rotational increment. The rotation is effected by a precision motor and each reading is integration from the detector for an interval. This would produce about 80 kilobytes of data, 10 k for each channel. This table could then be stored. In this instance, each "parameter" could be each channel of the scan.

As above, the data from a channel could then be transformed using a mathematical formula. For example, in a channel for the detection of scattering, in the fluxuation of light scatting during a coin rotation, the high and low points and the spacing between these points could be used for comparison to other data sets in data storage. This provides a rapid means for comparison that would not be dependent on the initial orientation of the scan about the diameter of the coin. The scan of the same coin rotated 90 degrees should produce the same pattern of low and high scatting measurements the same distance apart. This pattern would form the "coinprint".

The present invention is described above with reference to specific embodiments thereof. It will, however, be evident to a skilled artisan that various modifications and changes can be made thereto without departing from the broader spirit and scope of the present invention as set forth in the appended claims. For example, particular embodiments describe particular numbers recorded from particular rotational intervals. A skilled artisan will recognize that other measurement numbers may be used as well and combined in other ways. Further, the measurement values could be taken from values stepped over the coin in ways other than rotationally (e.g., on some defined grid or at defined locations spiraling outward or inward from a center or edge point of the coin, respectively).

These and various other embodiments are all within a scope of the present invention. The specification and drawings are, accordingly, to be regarded in an illustrative rather than a restrictive sense.

What is claimed is:

1. A method to develop an optical signature from a coin comprising:
    recording, using an optical instrument detecting light reflected or scattered from a surface of the coin as the coin is rotated, measurement values from the optical instrument of a plurality of optically detected parameters;
    processing the measurement values to produce a respective unique optically derived identifier for the coin for each of the plurality of optically detected parameters; and
    combining the respective optically derived identifiers into a searchable parameter that is parsable relative to the optically detected parameters.

2. The method of claim 1 wherein the measurement values of optically detected parameters include light scattering measurements from a linear detector array.

3. The method of claim 1 wherein the optically detected parameters include a scattering measurement.

4. The method of claim 1, wherein said processing includes identifying maximum and minimum levels relative to the measurement values for at least one of the optically detected parameters.

5. The method of claim 1 wherein each of the measurement values is obtained as related to a rotational position of the coin.

6. A method to develop an optical signature from a coin comprising:
    steering a beam of light across a surface of the coin through a predefined point, the predefined point being on a circular arc traceable on the surface of the coin as the coin is rotated through a rotational angle;
    collecting measurement values from an optical instrument responsive to light reflecting or scattering from the coin, as a function of the rotational angle of the coin;
    forming the optical signature from the measurement values such that the optical signature is unique to the coin and is parsable for at least one parameter measured by the optical instrument.

7. The method of claim 6 wherein the at least one parameter includes a height or a thickness of the coin as measured using optical profilometry.

8. The method of claim 6 wherein the at least one parameter includes an intensity level.

9. The method of claim 6 wherein the at least one parameter includes a spacing relating to a fluctuation of light scattering as the coin is rotated.

10. The method of claim 6 wherein the at least one parameter includes an interval integration of a light detector channel.

11. The method of claim 6 wherein the optical instrument includes a multichannel array of photo detectors.

12. The method of claim 6 wherein the beam of light is from an RGB light source.

13. The method of claim 6 wherein the beam of light is from a laser.

14. A method to develop an optical signature from a coin comprising:
    directing a line of light across a surface of the coin through a predefined point such that an optical instrument detects light reflecting or scattering from the coin;

rotating the coin successively to a plurality of rotation angles, the predefined point tracing a circle on the surface of the coin as the coin is rotated;

capturing measurement data from the optical instrument at each of the plurality of rotation angles of the coin; and processing the measurement data to produce the optical signature;

wherein the optical signature is separable into discrete values for each of a plurality of measured parameters relating to the light reflecting or scattering from the coin.

15. The method of claim 14 wherein one of the plurality of measured parameters is a height or a thickness of the coin determined from an optical profilometer.

16. The method of claim 14 wherein one of the plurality of measured parameters is a physical defect sensor mapping.

17. The method of claim 14 wherein one of the plurality of measured parameters is a surface color histogram.

18. The method of claim 14 wherein one of the plurality of measured parameters includes a plurality of high points of light scattering and a plurality of low points of light scattering and a spacing thereof.

19. The method of claim 14 wherein one of the plurality of measured parameters is an integration from a light detector for an interval over a rotational increment of the coin.

20. The method of claim 14 wherein the optical instrument includes a linear array of at least pairs of photo detectors.

* * * * *